United States Patent
Zeilkha

(10) Patent No.: US 12,226,442 B2
(45) Date of Patent: Feb. 18, 2025

(54) **COMPOSITION COMPRISING *NIGELLA SATIVA* OIL AND SURFACE-ACTIVE AGENTS**

(71) Applicant: N.S. OILS LTD., Kibbutz Sa'ad (IL)

(72) Inventor: Mor Zeilkha, Ramat Gan (IL)

(73) Assignee: N.S. OILS LTD., Kibbutz Sa'ad (IL)

( * ) Notice: Subject to any disclaimer, the term of this patent is extended or adjusted under 35 U.S.C. 154(b) by 869 days.

(21) Appl. No.: 17/291,545

(22) PCT Filed: Nov. 7, 2019

(86) PCT No.: PCT/IL2019/051221
§ 371 (c)(1),
(2) Date: May 5, 2021

(87) PCT Pub. No.: WO2020/095307
PCT Pub. Date: May 14, 2020

(65) Prior Publication Data
US 2021/0393727 A1    Dec. 23, 2021

Related U.S. Application Data

(60) Provisional application No. 62/757,187, filed on Nov. 8, 2018.

(51) Int. Cl.
| | |
|---|---|
| *A61K 36/71* | (2006.01) |
| *A61K 31/122* | (2006.01) |
| *A61K 47/22* | (2006.01) |
| *A61K 47/24* | (2006.01) |
| *A61P 3/04* | (2006.01) |
| *A61P 3/06* | (2006.01) |
| *A61P 9/12* | (2006.01) |

(52) U.S. Cl.
CPC ............ *A61K 36/71* (2013.01); *A61K 31/122* (2013.01); *A61K 47/22* (2013.01); *A61K 47/24* (2013.01); *A61P 3/04* (2018.01); *A61P 3/06* (2018.01); *A61P 9/12* (2018.01)

(58) Field of Classification Search
None
See application file for complete search history.

(56) References Cited

U.S. PATENT DOCUMENTS

2015/0004266 A1    1/2015    Babish

FOREIGN PATENT DOCUMENTS

WO    2011009862 A1    1/2011

*Primary Examiner* — Michael V Meller
(74) *Attorney, Agent, or Firm* — FISHERBROYLES, LLP; Roger L. Browdy

(57) ABSTRACT

The invention provides a composition comprising oil obtained from *Nigella sativa* seeds and one or more surface-active agents. Preferably, the concentration of thymoquinone in the composition is at least 2% (w/w), wherein the concentration of the surface-active agent(s) is at least 0.2% (w/w), and wherein the one or more surface-active agents are selected from the group consisting of D-α-Tocopherol polyethylene glycol succinate (TPGS), lecithin and isolecithin. The invention also provides a method for preventing and/or treating pathological states and disorders associated with obesity, comprising the steps of administering a composition of the invention to a human subject.

8 Claims, 12 Drawing Sheets

COMPOSITION COMPRISING *NIGELLA SATIVA* OIL AND SURFACE-ACTIVE AGENTS

FIELD OF THE INVENTION

The present invention is concerned with a composition that is suitable for use in the treatment and prevention of certain metabolic disorders which are often associated with obesity. More specifically, the present invention provides a composition comprising oil obtained *Nigella sativa* oil together with surface-active agents such as D-α-Tocopherol polyethylene glycol succinate (TPGS) and/or lecithin.

BACKGROUND OF THE INVENTION

Obesity is an increasingly common condition in many countries, and is associated with intense comorbidities, which can damage and shorten the lives of those suffering therefrom. These comorbidities include hypertension, atherosclerosis, increases in plasma HDL and LDL, fatty liver disease, and a dysfunctional adipocyte differentiation system.

Nonalcoholic fatty liver disorder (NAFLD) occurs with high fat diets, insulin resistance, obesity, and an unfavorable blood lipid profile. Individuals with NAFLD have a higher probability of developing metabolic syndrome, the worst form of which can advance to liver failure.

There are several compounds and agents that have been used to help mitigate the effects of obesity and other comorbidities such as metabolic syndrome. Examples of these substances are Cobalt porphyrin (CoPP), epoxyeicosatrienoic acid (EET) and L-4F. Other drugs used for comorbidities of obesity such as atherosclerosis, coronary artery disease, dyslipidemia, hypertension, and others are aspirin, statins, losartan and immunosuppressive agents, such as cyclosporine A. However, many of these treatment agents are associated with significant problems such as severe side-effects and high financial cost, preventing more widespread use.

Thus, despite the availability of agents such as those mentioned above for use in the treatment and prevention of obesity and its associated pathological states, a need exists for a composition that is highly effective and associated with a greatly reduced incidence of side effects. The present invention meets this need.

SUMMARY OF THE PRESENT INVENTION

In its most general form, the present invention is primarily directed to a composition comprising a combination of oil obtained from *Nigella sativa* seeds one or more surface-active agents.

While any suitable, bio-compatible surface-active agent may be used to prepare the composition of the present invention, preferably, said surface-active agents are selected from the group consisting of the vitamin E derivative, D-α-Tocopherol polyethylene glycol succinate (TPGS), lecithin and isolecithin.

Preferably, the composition of the present invention comprises oil obtained from *Nigella sativa* seeds and one or more surface-active agents, wherein the concentration of thymoquinone in said composition is at least 2% (w/w), wherein the concentration of said surface-active agent(s) is at least 0.2% (w/w), and wherein said one more surface-active agents are selected from the group consisting of D-α-Tocopherol polyethylene glycol succinate (TPGS), lecithin and isolecithin.

It is to be noted that thymoquinone is one of the major biologically-active components of *Nigella sativa* oil.

In one preferred embodiment, the composition of the present invention provides a composition comprises TPGS. In another preferred embodiment, the composition comprises lecithin. In still a further preferred embodiment, the composition comprises isolecithin.

The composition may also comprise a mixture of surface-active agents. Thus, in one embodiment, the composition comprises a combination of TPGS and lecithin. In another embodiment, the composition comprises a combination of TPGS and isolecithin. In a still further embodiment, the composition comprises a combination of lecithin and isolecithin.

Preferably, the composition comprises thymoquinone (one of the major components of *Nigella sativa* oil) at a concentration of at least 2% (w/w) and TPGS at a concentration of at least 0.2% (w/w).

In one preferred embodiment, the thymoquinone concentration of the composition is in the range of 2-6% (w/w) and the concentration of the one or more surface-active agents is in the range of 0.2-5% (w/w).

In another preferred embodiment, the concentration of thymoquinone in the composition is 3% (w/w) and the concentration of TPGS is 0.3%.

In another preferred embodiment, the concentration of thymoquinone in the composition is 3% (w/w) and the concentration of TPGS is 0.8%.

In a further preferred embodiment, wherein the composition comprises both TPGS and lecithin, the thymoquinone concentration is 3% (w/w), the TPGS concentration is 0.3% (w/w) and the lecithin concentration is 0.5% (w/w).

The invention also encompasses a method for treating and/or preventing pathological states and disorders associated with obesity, comprising the steps of administering a composition of the present invention to a human subject in need of such prevention and/or treatment. Said pathological disorders include, but are not limited to, increased systolic and/or diastolic blood pressure, increased blood glucose, increased blood levels of LDL-cholesterol, increased blood levels of oxidized LDL-cholesterol, reduced levels of HDL-cholesterol, impaired oxygen consumption, mitochondrial dysfunction and fatty liver disease.

The present invention is further directed to a composition of the present invention as disclosed herein for use in the treatment and/or prevention of pathological states and disorders associated with obesity.

DETAILED DESCRIPTION OF PREFERRED EMBODIMENTS

Figure 1A:
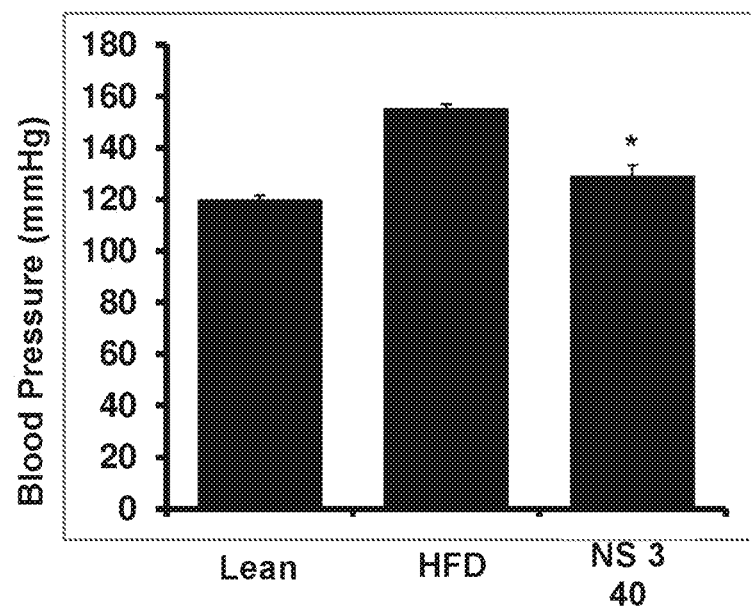
FIGS. 1*a* and 1*b* graphically show, respectively, the reduction in blood pressure, and the absence of effect on body weight, caused by administering a composition of the present invention to mice which have been treated with a high fat diet (HFD).

As explained hereinabove, the present invention is directed to a composition comprising *Nigella sativa* oil together with one or more surface-active agents. In particularly preferred embodiments of the invention, these agents are selected from the group consisting of TPGS, lecithin and isolecithin. It is to be noted that the term 'isolecithin', as used in the context of the present disclosure refers to hydrolyzed or partially-hydrolyzed lecithin.

The thymoquinone-containing *Nigella sativa* oil used to prepare the present invention may be obtained from any of the several different commercial sources (e.g. N. S. Oils, Kibbutz Sa'ad, Israel). Preferably, the oil is a cold pressed oil obtained from *Nigella sativa* seeds using a screw-driven oil press. It is to be noted that the species *Nigella sativa* is also known by a variety of common names including (but not limited to) black cumin, black caraway, fennel, nigella, nutmeg flower, and roman coriander.

TPGS is a water-soluble derivative of the natural form of vitamin E, d-α-tocopherol. This substance is usually produced by the esterification of crystalline d-α-tocopheryl succinate with a polyethylene glycol (e.g. polyethylene glycol 1000) and may be obtained from several different commercial suppliers. Similarly, lecithin and isolecithin (both of which may originate from natural sources such as sunflower gum) may be readily obtained from commercial suppliers.

The composition may be prepared by dissolving the required amount of TPGS and/or other surface-active agents into the cold pressed oil. The composition may further comprise other active ingredients, such as other plant extracts, vitamins, minerals, food supplements and so on. Also, the composition of the present invention may further comprise additional substances that improve the bioavailability of the main biologically-active components of said composition. Commercially-available examples of such bioavailability-improving substances include piperine and bioperine.

The composition may further comprise pharmacologically inactive ingredients such as excipients of various kinds, in order to prepare the dosage forms mentioned hereinabove.

In the methods of the present invention disclosed hereinabove, the composition comprising the aforementioned active components is preferably administered orally. In other embodiments, the composition may be administered by different routes including, but not limited to, topically, intravenously and intramuscularly.

The compositions of this aspect of the present invention may be formulated in several different dosage forms for administration to human subjects by the routes indicated hereinabove. Suitable dosage forms include (but are not limited to) oral dosage forms, sub-lingual dosage forms, injectable formulations, suppositories, patches for use on skin or mucous membranes, inhalable formulations, topical formulations and so on. Further details of the preparation of such formulations and dosage forms can be obtained from any standard reference on the subject, such as Remington's Pharmaceutical Sciences, Mack Publishing Co, Easton, Pa, USA, $21^{st}$ edition (2006).

The composition of the present invention may also be added directly to foodstuffs or beverages, either during their manufacture or to the finished products, in the form of food additives.

In the methods of the present invention, the composition may be administered once daily or several times (e.g. twice or three times) daily.

As disclosed hereinabove, the method of the present invention encompasses the treatment and/or prevention of various pathological states and disorders that are "associated with obesity". It is to be emphasized that although the above-mentioned exemplary pathological states and disorders are indeed, in many cases, found in obese individuals, they may also occur in overweight (but not obese) individuals, normal weight individuals and even underweight individuals. Thus, the presently disclosed and claimed method also includes the prevention and/or treatment of said pathological states and disorders even when they occur in non-obese subjects. In other words, the phrase "pathological states and disorders associated with obesity" is used to identify to those states and disorders which are commonly seen in obese individuals (both in humans and in other mammalian species), without restricting the claimed method to the treatment and prevention of said states and disorders in subjects which are actually obese. Thus, for example, the method of the present invention could be used to treat or prevent the indicated states and disorders in individuals who are of normal weight, lower than normal weight, overweight or obese.

The beneficial therapeutic and preventative effects of the composition of the present invention are demonstrated in the following non-limiting working examples.

EXAMPLES

General Methods

In the studies reported below, eight-week old C57B16 male mice were put on a high fat diet (HFD) for 20 weeks, a time frame in which signs of obesity and cardiovascular disease start to occur. Mice were divided into four groups of six animals each. 1) control group—normal chow diet; 2)

HFD; 3) HFD, treated orally for the final 8 weeks with a composition of the present invention (referred to in the figures and description that follows as "NS3") at a daily dosage of 26 mg/kg. Said composition comprised cold-pressed *Nigella sativa* oil obtained from N. S. Oils, Sa'ad, Israel containing 3% thymoquinone and 0.3% TPGS.

During the course of the experiment, various parameters (blood glucose levels, blood lipid levels, oxygen consumption and body weight) were measured as described hereinbelow.

After 20 weeks, the mice were sacrificed, their abdominal cavities opened by ventral incision and internal organs removed and centrifuged. The material thus obtained was then subjected to gel electrophoresis and western blotting, and real time PCR, in order to measure levels of protein expression. All animal experiments followed the NYMC IACUC institutionally approved protocol in accordance with the NIH guidelines.

Statistical Analysis

Statistical significance between the results obtained for the HFD mice group, the group of HFD mice subject treated with the composition of the present invention and the control group mice was determined using the Student t-test for pairwise comparison between groups or via ANOVA with Tukey-Kramer analysis for comparison between multiple groups. Data are shown as mean values±S.E.M. Bonferroni's post-test analysis or multiple comparisons was used to calculate the significance of mean value differences using a one-way analysis of variance. The null hypothesis was not accepted at $p<0.05$.

Example 1

Effect of the Composition of the Present Invention on Body Weight and Blood Pressure in Obese Mice Methods The animals used in the study, the composition of the present invention used, and the experimental protocol are all as disclosed hereinabove in 'General methods'. Blood pressure measurements in the mice were made using the tail cuff method, as well known in the art.

Results

Induction of Black Seed Oil Significantly Decreases Blood Pressure while Keeping the Weight the Same.

Figure 1B:
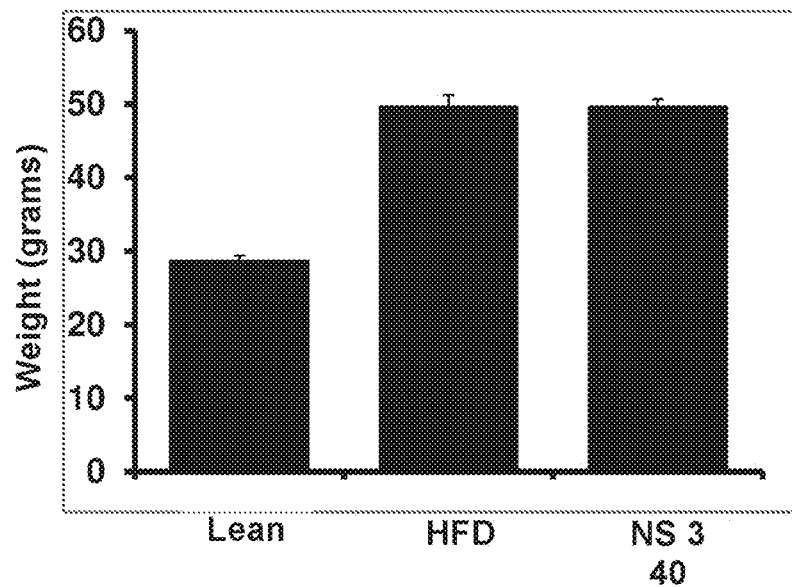

Blood pressure went down ($p<0.05$) after the introduction of the composition of the present invention (FIG. 1a). These results show that the vessels in the blood are relaxing, allowing more blood to flow and therefore impeding the process of heart failure due to more blood being able to flow. It also helps prevent myocardial infarctions by helping to slow down the heart rate of the mice, as shown by the vasodilation, which allows the heart to work less hard and therefore become less tired. It does not affect weight in any significant way (as shown in FIG. 1b), indicating that the mice are still obese but are starting to show signs of reduced comorbidities.

Example 2

Effect of the Composition of the Present Invention on Blood Glucose, Blood Lipid Levels and Oxygen Consumption in Obese Mice Methods The animals used in the study, the composition of the present invention used, and the experimental protocol are all as disclosed hereinabove in 'General methods'. Fasting blood glucose as well as levels of LDL-C and oxidized LDL-C (ox-LDL) were measured in blood taken from the tail vein following a six hour fast.

Oxygen Consumption (V02) in the mice was determined using the following method: The mice were allowed to adjust to the oxygen consumption chambers for a total of 3 weeks. Accommodation periods for the 3-week duration were executed in 2 hour increases, triweekly. The Oxylet gas analyzer and air flow unit (Oxylet; Panlab-Bioseb, Vitrolles, France) were used to determine VO2. Each mouse was placed individually in the machine and VO2, VCO2 and respiratory quotient (RQ; VCO2/VO2) were measured.

Results

Usage of Black Seed Oil, Significantly Decreases Blood Glucose, Significantly Decreases LDL and Oxidized-LDL (ox-LDL), and Significantly Increases VO2

Figure 2A:
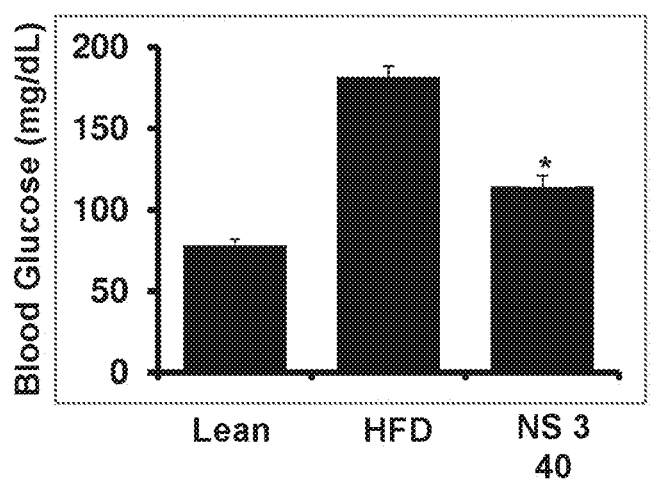
FIG. 2*a* graphically shows the significant reduction in blood sugar in HFD mice following treatment with a composition of the present invention.

Obese mice treated with the composition of the present invention had significant reduction in their blood sugar levels, as compared with the untreated obese mice (HFD-high fat diet only; $p<0.05$), as shown in FIG. 2a. These results indicate that the composition of the present invention may be used to treat diabetes mellitus, a metabolic disorder often (but not always) associated with obesity.

Figure 2B:
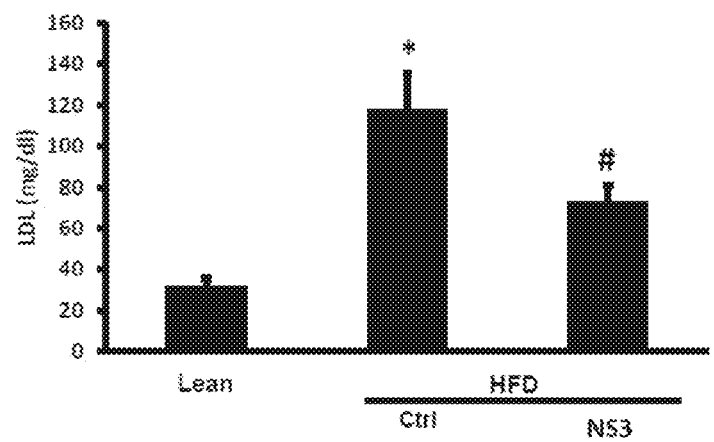
FIGS. 2*b* and 2*c* graphically show, respectively, the significant reduction in LDL and Ox-LDL levels in HFD mice treated with a composition of the present invention.
Figure 2C:
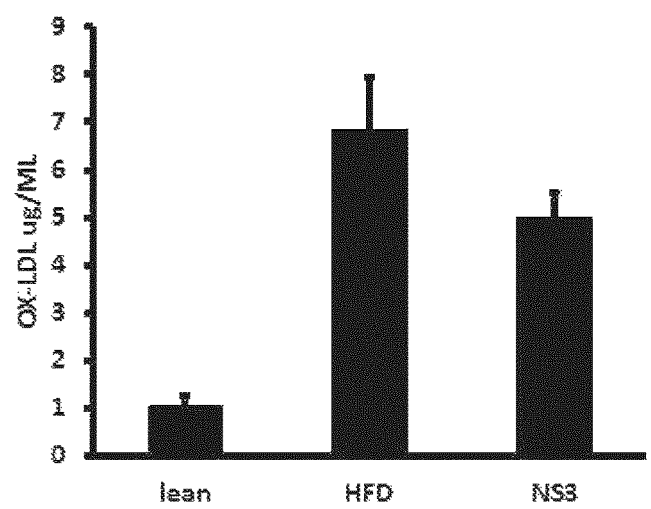

Obese mice treated with the composition of the present invention also show significant reductions ($p<0.05$) in both LDL (FIG. 2b) and Ox-LDL (FIG. 2c), when compared from their non-treated obese counterparts (HFD). These results indicate that the composition of the present invention may be used to treat, reverse and/or prevent the development of adverse blood lipid profiles that are associated with coronary artery disease and other atherosclerotic pathologies.

Figure 2D:
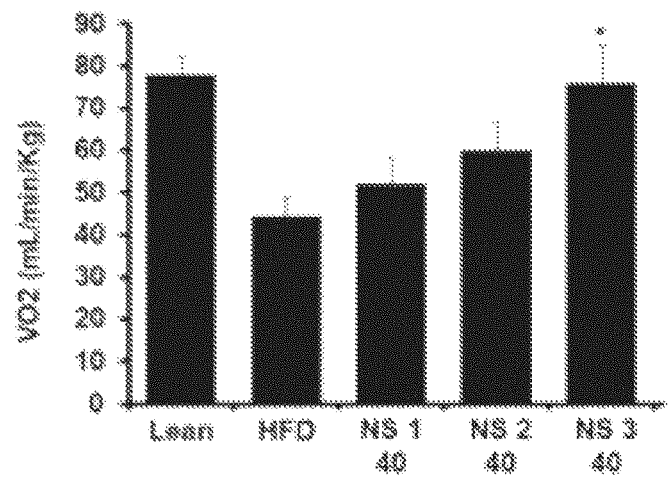
FIG. 2*d* graphically presents data showing the significant increase in oxygen consumption in HFD mice treated with a composition of the present invention.

FIG. 2d summarizes the oxygen consumption results obtained from this study. In addition to the lean control and untreated high fat diet (HFD) groups, this study compared the effect of three different *Nigella sativa* oil compositions on oxygen consumption: NS1 (cold-pressed oil containing 3% (w/w) thymoquinone without any additional components), NS2 (cold-pressed oil containing 3% (w/w) thymoquinone and 2% (w/w) Giralec HE-60 (a surface active agent derived containing sunflower lecithin) and NS3 (the composition of the present invention). It may be seen from this figure that only the composition of the present invention (NS3) caused a statistically significant increase in oxygen consumption ($p<0.05$) when compared with the untreated high fat diet (HFD) group. These results suggest that the composition of the present invention may be useful in increasing the oxygenation of subjects suffering from some of the metabolic and cardiovascular disorders that are both associated with obesity and seen in some non-obese subjects.

Example 3

Effect of the Composition of the Present Invention on the Expression of OPA1, MFN-1 and MFN2 Gene Products in Obese Mice

Methods

The animals used in the study, the composition of the present invention used, and the experimental protocol are all as disclosed hereinabove in 'General methods'.

Real Time PCR

Real Time PCR was used to measure the expression of the OPA1, MFN1 and MFN2 genes, by means of first running transcription in reverse and then multiplying the resultant DNA and then measuring the presence of the genes in the sample.

Western Blot Analysis and Protein Expression

For protein expression analyses, mitochondria had their membranes broken down in RIPA lysis buffer supplemented with protease and phosphatase inhibitors (Complete™ Mini and PhosSTOP™, Roche Diagnostics, Indianapolis, IN as previously described [E,29,37]. NOV protein levels were deduced by Western Blot and were normalized to transferrin protein. The OPA1, MFN1 and MFN2 proteins were also measured. β-actin was used to show that the western blot is working properly for mitochondrial analysis.

Results

The Composition of the Present Invention Significantly Increases the Expression of the OPA1, MFN1 and MFN2 Proteins.

Figure 3A:
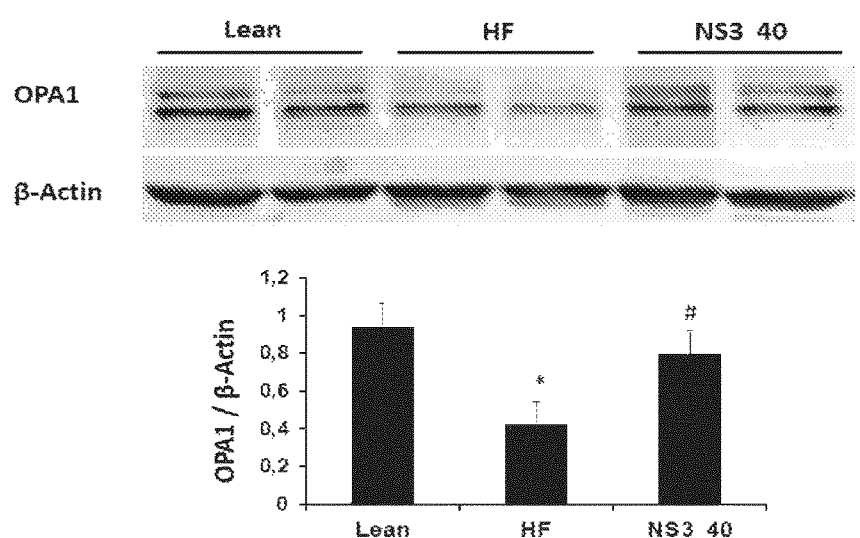
FIGS. 3a-3c present data showing the increased expression of the OPA1, MFN1 and MFN2 gene products in HFD mice treated with a composition of the present invention.
Figure 3B:
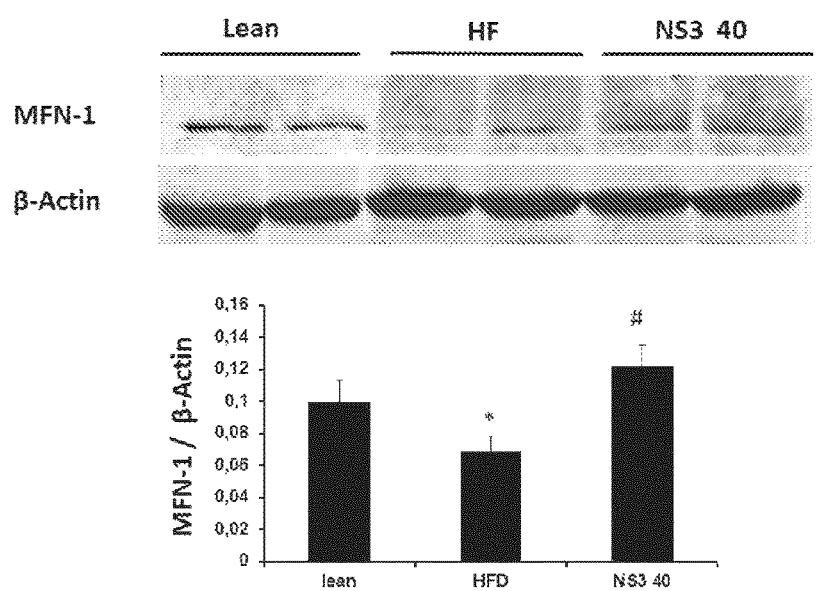
Figure 3C:
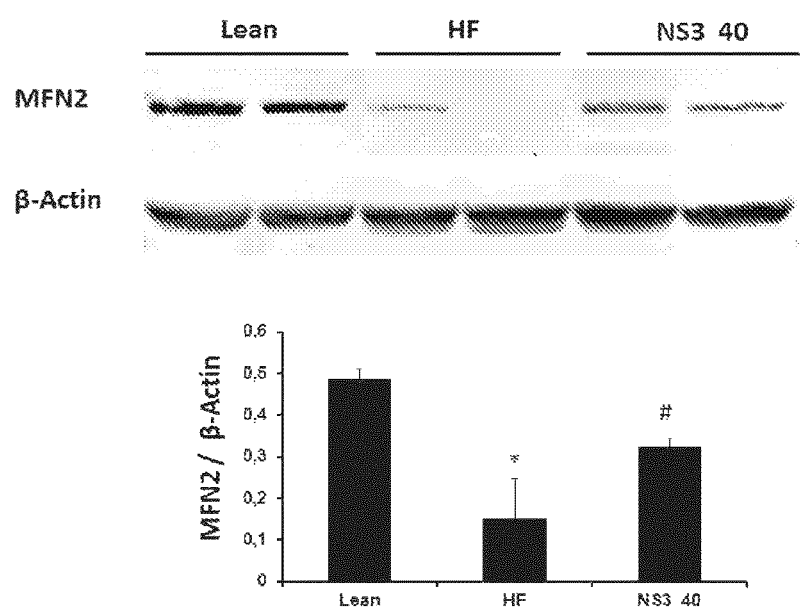

Compared with obese mice, obese mice fed with the composition of the present invention show increased expression of proteins by the OPA1, MFN1 and MFN2 genes ($p<0.05$)(FIGS. 3a-3c).

The OPA1 gene encodes a mitochondrial dynamin-like protein that is responsible for regulating mitochondrial fusion in the inner mitochondrial membrane, thereby contributing to ATP synthesis. Similar functions are also attributed to the proteins expressed by the MFN1 and MFN2 genes. These results therefore suggest that the composition of the present invention is capable of improving impaired energetic processes in the mitochondria and may therefore assist in the treatment and prevention of metabolic disorders that are associated both with obesity and with a decrease in energy production.

Example 4

Effect of the Composition of the Present Invention on the Expression of NOV, HO-1 and HO-2 Gene Products in Obese Mice

Methods

The animals used in the study, the composition of the present invention used, and the experimental protocol are all as disclosed hereinabove in 'General methods'. Real time PCT and western blot analysis were performed as described in Example 3, in order to measure the expression of the NOV, HO-1 and HO-2 genes in tissue obtained from the abdominal cavity of the mice used in this study.

Results

Black Seed Oil Significantly Decreases NOV Presence, while not Significantly Affecting HO-1 or HO-2 Presence.

Figure 4A:
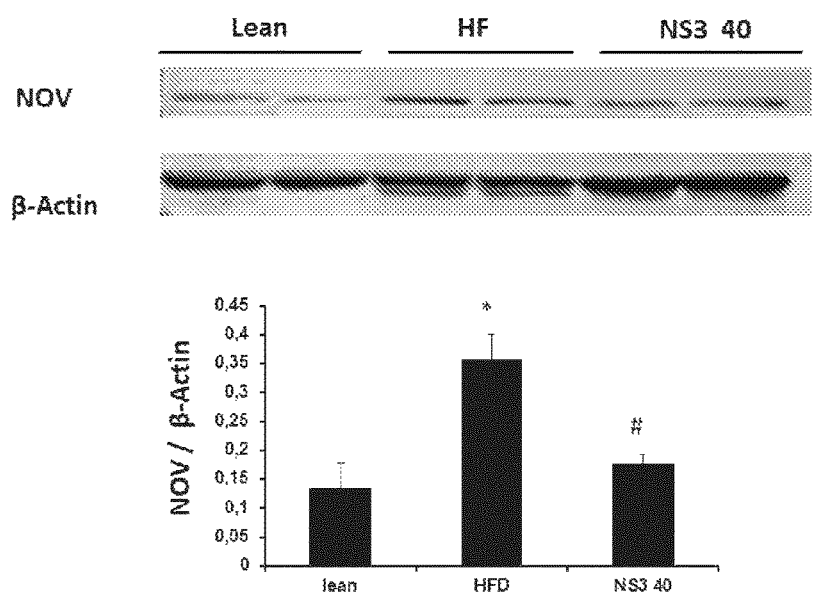
FIG. 4a presents data showing the significant decrease in NOV gene expression in HFD mice treated with a composition of the present invention.

Obese mice treated with the composition of the present invention display a significantly decreased level of NOV expression ($P<0.05$), as compared to untreated obese mice (HFD), as shown in FIG. 4a. The NOV gene product is a protein that causes inflammation and therefore impedes body function in many areas if in excess. Obese individuals have excessive levels of this protein, causing many comorbidities. The present results suggest that treatment with the composition of the present invention may inhibit the development of these disorders.

Figure 4B:
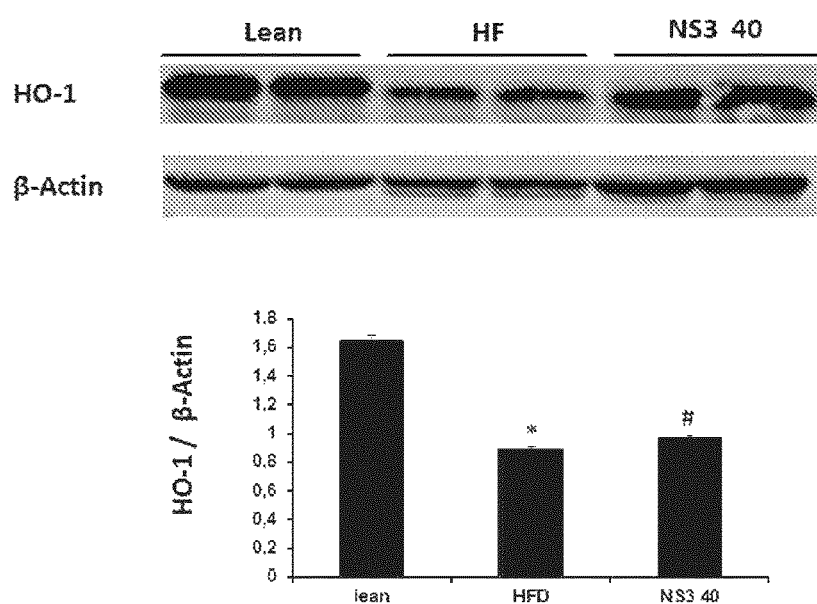
FIGS. 4b and 4c present data showing an absence of any effect following treatment of HFD mice with a composition of the present invention on, respectively, the expression of the HO-1 and HO-2 genes.
Figure 4C:
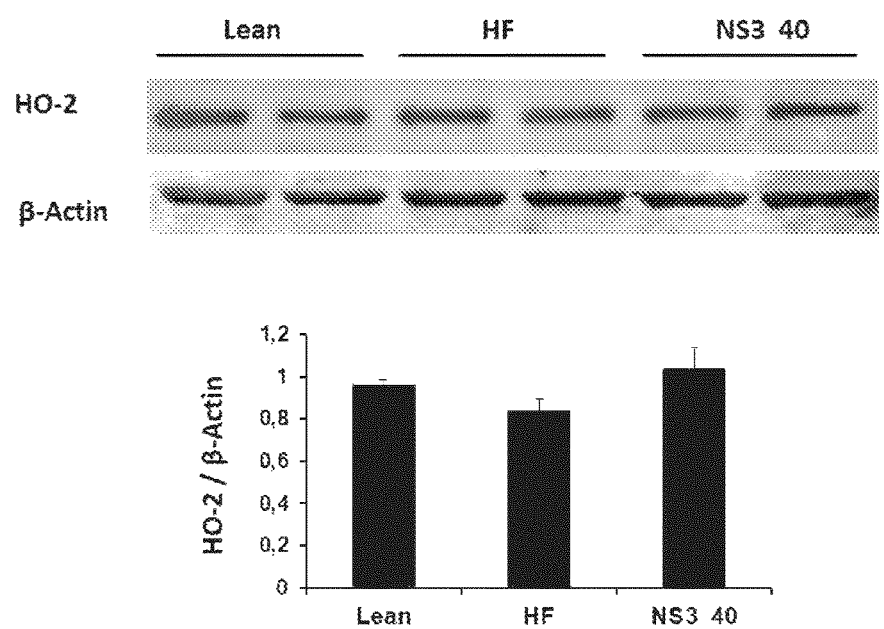

Obese mice treated with the composition of the present invention, as compared to obese mice sans black seed oil, do not show a significantly increased expression of either HO-1 or HO-2 (FIG. 4b,4c).

Example 5

Effect of the Composition of the Present Invention on the Percentage of Fat and Liquid Fat Droplet Diameter the Livers of Obese Mice

Methods

The animals used in the study, the composition of the present invention used, and the experimental protocol are all as disclosed hereinabove in 'General methods'. It is to be noted, however, that two different treatment groups were included in this study: one group received treatment with a composition of the present invention comprising 3% thymoquinone (3% TQ, in the figures), while a second group received a composition comprising *Nigella saliva* oil containing 0.3% TPGS and 1% thymoquinone (1% TQ). Samples of the livers of the sacrificed animals at the end of the study were sectioned and lipid droplet diameter and fat percentage in the liver were determined. In addition, the degree of fibrosis in the liver was also determined using histological methods.

Results

Figure 5A:
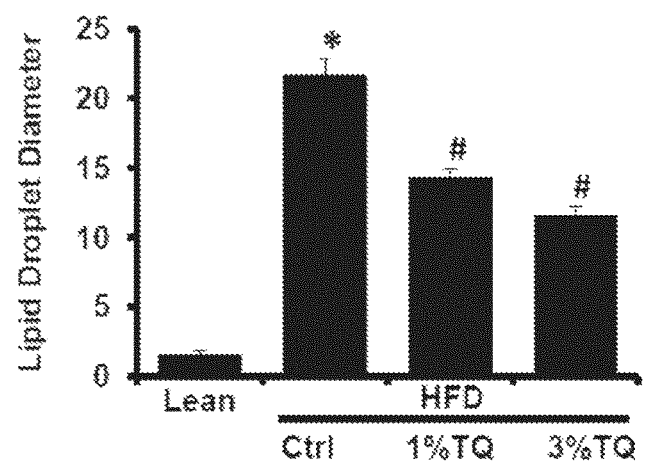
FIG. 5a graphically shows the effect of treatment with a composition of the present invention (3% TQ) and a composition having a 1% TQ concentration (comparative) on liquid drop diameter in in the livers of HFD mice.

As shown in FIG. 5a, both the composition of the present invention (3% TQ) and the same composition having a reduced thymoquinone content (1% TQ) caused a significant ($p<0.05$) reduction in lipid droplet diameter, as compared with the untreated high fat diet (HFD) group. The treatment with the composition of the invention, however, caused a greater decrease than that caused by the reduced-thymoquinone composition.

Figure 5B:
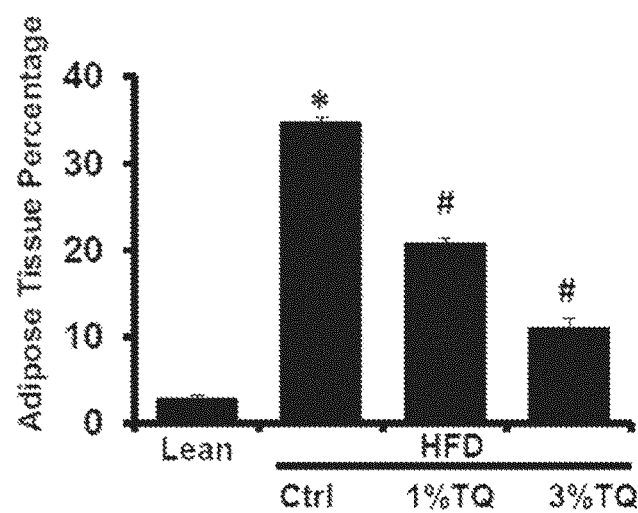
FIG. 5b graphically shows the effect of treatment with a composition of the present invention (3% TQ) and a composition having a 1% TQ concentration (comparative) on the percentage of adipose tissue in the livers of HFD mice.

Similarly, as shown in FIG. 5b, the percentage of adipose tissue in the liver samples was significantly reduced by both treatment protocols, when compared with the untreated HFD control. Again, the effect due to the composition of the present invention (having a thymoquinone concentration of 3%) was much more pronounced than the result seen with the 1% thymoquinone composition.

Figure 5C:
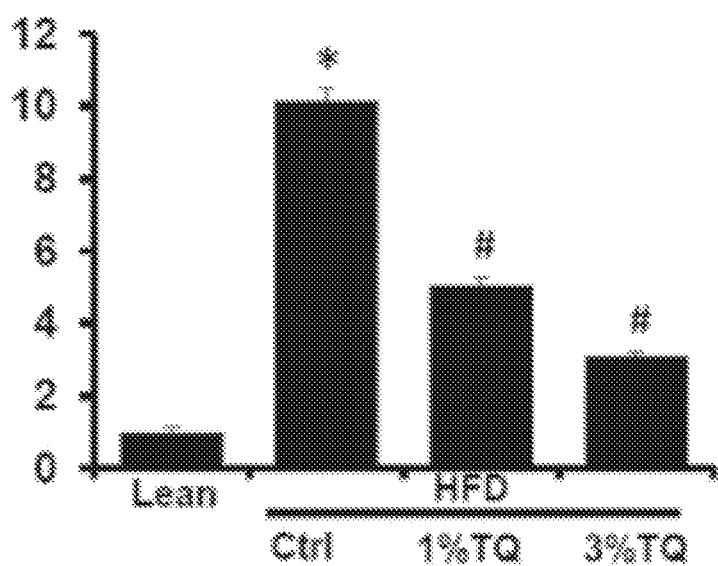
FIG. 5c graphically shows the effect of treatment with a composition of the present invention (3% TQ) and a composition having a 1% TQ concentration (comparative) on the amount of fibrosis in the livers of HFD mice.

FIG. 5c presents results for the degree of fibrosis of the liver samples taken from the various groups of mice. As seen, both treatment groups significantly reduced the amount of fibrosis as compared with the untreated HFD group, with the greatest effect being seen with the composition of the present invention (3% TQ).

Figure 6:
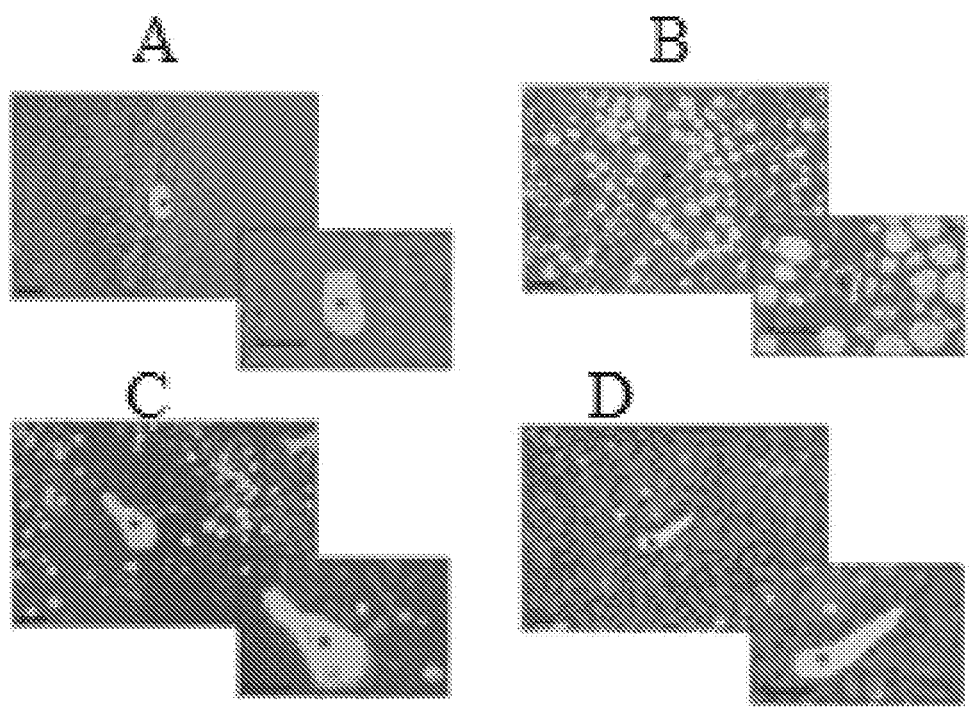
FIG. 6 presents photographs of stained histological sections of livers taken from mice assigned to the following treatment or control groups: A (lean, untreated); B (HFD, untreated); C (HFD, treated with a 1% TQ composition (comparative); and D (HFD, treated with a composition of the present invention).

Histological sections of the mice livers taken from the various treatment and control groups are shown in FIG. 6, in both low power and enlarged, high power views. Thus, panel A is a section taken from the liver of a lean (i.e. negative control) animal, while panel B is taken from a mouse in the HFD group. Both the size and number of the lipid droplets is clearly far greater in the liver sections prepared from the HFD animals than those obtained from the lean individuals. Panel C is a section taken from the liver of an HFD mouse treated with a composition similar to that of the present invention but comprising a reduced concentration (1%) of TQ, while panel D is taken from an HFD mouse treated with a composition of the present invention containing 3% TQ. It is clear from a comparison of these two latter panels that the 3% TQ preparation (i.e. the composition of the present invention) has reduced both the size and number of lipid droplets to a far greater degree than the 1% TQ preparation.

All of the results in this part of the study strongly support a role for the composition of the present invention in preventing and/or treating fatty liver disease, and other hepatic disorders associated with obesity and metabolic syndrome.

The results obtained in all of the studies reported in the Examples hereinabove indicate that the composition of the present invention is able to prevent mitochondrial dysfunction in obese subjects, by increasing the expression of the fusion proteins as OPA1, MFN1 and MFN2, as well as decrease the pro-inflammatory protein NOV. On a different level, the composition was also shown to improve the health of obese mice by decreasing Blood Glucose, Blood Pressure, LDL and OX-LDL and increasing Oxygen Consumption. Therefore, taken together, these results indicate that the composition of the present invention is effective in delaying the progression of chronic renal, heart and liver diseases, and may be used for prevention and/or treatment care in obesity, and in non-obese patients suffering from various metabolic and cardiovascular disorders.

The invention claimed is:

1. A composition suitable for treating high blood pressure, comprising synergistically effective amounts of thymoquinone (TQ) from *Nigella sativa* oil; D-α-Tocopherol polyethylene glycol succinate (TPGS); and isolecithin and/or lecithin.

2. The composition according to claim 1, comprising TQ, TPGS and lecithin.

3. The composition according to claim 1, comprising TQ, TPGS and isolecithin.

4. The composition according to claim 1, comprising TQ, TPGS, lecithin and isolecithin.

5. The composition according to claim 1, wherein the thymoquinone concentration is in the range of 2-6% (w/w) and the concentration of TPGS and isolecithin and/or lecithin is in the range of 0.2-5% (w/w).

6. The composition according to claim 1, wherein the thymoquinone concentration is 3% (w/w) and the TPGS concentration is 0.3% (w/w).

7. The composition according to claim 2, wherein the thymoquinone concentration is 3% (w/w), the TPGS concentration is 0.3% (w/w) and the lecithin concentration is 0.5% (w/w).

8. A method for treating high systolic blood pressure, high diastolic blood pressure, diabetes mellitus, adverse LDL-C and oxo-LDL lipid profile, or fatty liver disease in a human in need thereof, comprising administering an effective amount of the composition of claim 1 to a human in need thereof.

* * * * *